United States Patent [19]

Ishikawa et al.

[11] Patent Number: 5,387,109
[45] Date of Patent: Feb. 7, 1995

[54] FRUCTOSYLAMINE DEGLYCASE AND A METHOD OF PRODUCING IT

[75] Inventors: Atsushi Ishikawa; Yoshifumi Ohshima; Mikio Yamada; Hajime Okumura, all of Handa; Yoshiya Kawamura, Kohnan, all of Japan

[73] Assignee: Nakano Vinegar Co., Ltd., Handa, Japan

[21] Appl. No.: 66,499

[22] Filed: May 24, 1993

[30] Foreign Application Priority Data

Jun. 5, 1992 [JP] Japan .................................. 4-169938
Sep. 25, 1992 [JP] Japan .................................. 4-279292

[51] Int. Cl.$^6$ .......................... C12N 9/04; C12N 9/06; C12N 9/08
[52] U.S. Cl. ..................................... 435/191; 435/189; 435/190; 435/192; 435/200; 435/254.22; 435/26; 435/71.1; 435/71.2
[58] Field of Search .................... 435/189, 190, 254.22, 435/26, 191, 192, 200, 71.1, 71.2

[56] References Cited

FOREIGN PATENT DOCUMENTS 61-268178 11/1986 Japan .
3-155780 7/1991 Japan .
4-4874 1/1992 Japan .

OTHER PUBLICATIONS

Horiuchi et al., *Agric Biol Chem* 55(2) pp. 333–338, 1991.
Horiuchi et al., *Agric Biol Chem* 53(1) pp. 103–110, 1989.
Roger N. Johnson et al., "Fructosamine: a new approach to the estimation of serum glycosylprotein. An index of diabetic control", Clinica Chimica Acta, 127 (1982) pp. 87–95.
Hawk et al., "Biological/Biomedical Applications of Liquid Chromatography", Marcel Dekker, Inc., 1979, pp. iii–ix and 659–677.
N. J. W. Kreger-van Rij, The yeasts a taxonomic study, Elsevier Science Publishers B.V.–Amsterdam, 1984, Title page, pp. XII–XVI, 1, 10, 36, 37, 56–60, 75, 76, 84, 85, 89, 329, 330, 585–587, 591, 592, 601, 602, 692–694, 998–1003.
Database WPI, Section Ch, Week 8704, Derwent Publications Ltd., London, GB; AN 87-024756 of JP-A-61 280 297 (Noda Inst Sci Res) Dec. 10, 1986.

*Primary Examiner*—Douglas W. Robinson
*Assistant Examiner*—Leon Blaine Lankford
*Attorney, Agent, or Firm*—Frishauf, Holtz, Goodman & Woodward

[57] ABSTRACT

Disclosed are a novel fructosylamine deglycase characterized by the specificity to amadori compounds of catalyzing oxidation of the compounds to produce an $\alpha$-ketoaldehyde, an amine derivative and hydrogen peroxide; a method of producing the novel enzyme by cultivating microorganisms belonging to the genus Candida and having an ability of producing the novel enzyme; and a method of quantitative determination of amadori compounds by applying the novel enzyme to a sample containing amadori compounds to measure the amount of the hydrogen peroxide to be formed by the oxidation reaction or measure the amount of the oxygen to be consumed by the reaction to thereby obtain the amount of the amadori compounds from the measured value. The invention provides a novel enzyme characterized by the high specificity to the reaction with amadori compounds, especially that having therein a saccharide moiety as bonded to the $\epsilon$-amino group, and also provides a method of producing the enzyme and a method of quantitative determination of amadori compounds with the enzyme. Using the enzyme, quantitative determination of amadori compounds, which is difficult by conventional enzymatic methods, is possible with ease. In particular, in measurement of the amount of a saccharified protein in a sample from a living body, which is an important index substance in diagnosis of diabetes, the enzymatic method of the invention of measuring fructosamine in the sample is hardly influenced by other interfering substances or impurities in the sample, the influence by them having been inevitable in conventional chemical methods. Accurate determination of the amount is possible by the method, and the method is free from the inconvenience of staining the kits and instruments used. For measuring glycohemoglobin, the method displays another characteristic feature that its operation is more simple and needs less labor and time than conventional methods.

5 Claims, 6 Drawing Sheets

FRUCTOSYLAMINE DEGLYCASE AND A METHOD OF PRODUCING IT

FIELD OF THE INVENTION

The present invention relates to a novel enzyme fructosylamine deglycase and a method of producing it and also to a method of quantitative determination of amadori compounds in a sample using the enzyme.

BACKGROUND OF THE INVENTION

The amadori compounds as referred to herein are compounds to be formed by non-enzymatic reaction of a reducing sugar aldose and an amino group-containing compounds followed by an Amadori rearrangement of the reaction product. For instance, it is known that in a substance containing large amounts of saccharides, amino acids and proteins, such as soy sauce, miso (fermented soybean paste) or the like, the amino acids are saccharified into amadori compounds in accordance with the fermentation time and the storage time and the amadori compounds play an important role in the browning of foods and in the changing of flavor components. Also in living bodies, fructosylamine compounds of amadori compounds having a glucose and an amino group as bonded to each other are formed. For instance, fructosylamine compounds formed by saccharification of hemoglobin in blood with glucose are called glycohemoglobin, and fructosylamine compounds formed by the reaction of albumin in serum and glucose are called fructosamine. These are indicated to have physiological meanings in the clinical field as indices to show average blood glucose level in diabetics, and these are explicitly measured for the diagnosis of diabetes.

There is known a method of measuring glycohemoglobin by high performance liquid chromatography (Chromatogr. Sci., Vol. 10, 659 (1979)), but the method has many drawbacks since the performance in operation and the accuracy in measurement are unsatisfactory and expensive appliances are needed. As a method of measuring fructosamine, there is known a method of measuring it by coloration of a dye by utilizing the reducing property of the fructosylamine compounds under an alkaline condition (Clin. Chem. Acta., Vol. 127, 87 (1982)) and the method has heretofore been used broadly. However, the method also has many drawbacks since the specificity of the reaction is unsatisfactory and the dye used often stains the cell during the measurement. Under the above-described situation, a novel measuring method free from such drawbacks is desired.

As enzymes of decomposing amadori compounds, for example, there have heretofore been known fructosylamino acid oxidase to be produced by microorganisms belonging to the genus Corynebacterium (Japanese Patent Application Laid-Open No. 61-268178), fructosylamine oxidase to be produced by microorganisms belonging to the genus Aspergillus (Japanese Patent Application Laid-Open No. 3-155780) and fructosylamino acid decomposing enzyme to be produced by microorganisms belonging to the genus Penicillium (Japanese Patent Application Laid-Open No. 4-4874). However, in order to quantitatively determine the fructosylamine compounds in foods or living bodies, an enzyme which acts not only on the amadori compounds to be formed by reaction with the α-amino group of an amino acid but also especially on the amadori compounds to be formed by reaction with the ε-amino group of it is important. However, the known enzymes have weak activity so that quantitative determination of a minor amount of amadori compounds was difficult to determine.

SUMMARY OF THE INVENTION

The present inventors earnestly investigated so as to develop a satisfactory method of quantitative determination of amadori compounds with an enzyme.

The present inventors searched broadly various natural microorganisms so as to find out an enzyme having an activity of decomposing amadori compounds and, as a result, have found that a strain of microorganisms of belonging to the genus Candida may produce an enzyme which acts extremely sufficiently not only on amadori compounds to be formed by reaction with the α-amino group of an amino acid but also especially on an amadori compound to be formed by reaction with the ε-amino group of an amino acid. On the basis of the finding, they have completed the present invention.

The first aspect of the present invention is to provide a fructosylaminedeglycase having the following physico-chemical properties:

(a) effect and substrate specificity:

the enzyme acts on amadori compounds, especially effectively on an ε-amino acid derivative thereof to catalyze oxidation of the compound to produce an α-ketoaldehyde, an amine derivative and hydrogen peroxide;

(b) optimum pH and pH stability:

the enzyme is stable at a pH range of from 5.0 to 8.0 to a substrate of di-fructosyl-lysine, and the optimum pH range of it to the substrate is from 7.0 to 8.0 (in a phosphate buffer);

(c) range of reaction temperature:

the range of the reaction temperature of the enzyme is from 15° to 45° C.;

(d) thermostability:

the enzyme is stable to heat treatment of 40° C. for 10 minutes, and when it is heated at 50° C. for 10 minutes, 80% or more of it is inactivated;

(e) molecular weight:

the enzyme has a molecular weight of about 43000, as measured by gel filtration on Toyo Pearl HW-55F (a porous, semirigid, spherical gel) column.

The second aspect of the present invention is to provide a method of producing a fructosylamine deglycase having the above-mentioned physico-chemical properties, by cultivating microorganisms belonging to the genus Candida and having a capacity of producing the fructosylamine deglycase in a medium followed by collecting the produced fructosylamine deglycase from the culture.

The third aspect of the present invention is to provide a method of quantitative determination of amadori compounds in a sample containing the compounds by applying the fructosylamine deglycase having the above-mentioned physico-chemical properties to a sample containing amadori compounds followed by measuring the amount of the hydrogen peroxide to be formed by the oxidation reaction or measuring the amount of the oxygen to be consumed by the reaction and obtaining the amount of the amadori compounds from the measured value.

DETAILED DESCRIPTION OF THE INVENTION

The physico-chemical properties of the fructosylamine deglycase of the present invention are mentioned below.

(1) Method of Determination of the Titer of the Enzyme

The following Method 1 and Method 2 are mentioned for colorimetric determination of hydrogen peroxide to be formed by the action of the enzyme.

Method 1

0.1 ml of 1 mM di-fructosyl-lysine (as dissolved in 0.05M phosphate buffer pH 7.0) is added to 0.4 ml of 0.05M phosphate buffer (pH 7.0) containing 0.3 mM 4-aminoantipyrine, 0.5 mM N-ethyl-N-(2-hydroxy-3-sulfopropyl)-m-toluidine (TOOS) and 2.0 U/ml peroxidase, and the temperature of the resulting system is equilibrated at 37° C. To this is added 0.06 ml of the enzyme solution having a suitable activity, whereupon the variation of the absorbance of the system is measured with a spectrophotometer (U-2000 Model, manufactured by Hitachi Ltd. ). From the calibration curve as formed from a standard solution containing a determined amount of hydrogen peroxide to indicate the relation between the variation of the absorbance and the amount of hydrogen peroxide, the amount of the hydrogen peroxide as formed in the test system is obtained. The amount of the enzyme of forming one micromole of hydrogen peroxide per one minute is defined to be one activity unit.

Method 2

0.2 ml of 1 mM di-fructosyl-lysine (as dissolved in 0.05M phosphate buffer pH 7.0) is prepared, and the temperature of it is equilibrated at 37° C. To this is added 0.12 ml of the enzyme solution having a suitable activity and reacted for a suitable period of time at 37° C., and the reaction is stopped in a hot water bath of 100° C. To this is added 0.8 ml of 0.05M phosphate buffer (pH 7.0) containing 0.3 mM 4-aminoantipyrine, 0.5 mM TOOS and 2.0 U/ml peroxidase, whereupon the variation of the absorbance of the system is measured with a spectrophotometer (U-2000 Model, manufactured by Hitachi Ltd. ). From the calibration curve as formed from a standard solution containing a determined amount of hydrogen peroxide to indicate the relation between the variation of the absorbance and the amount of hydrogen peroxide, the amount of the hydrogen peroxide as formed in the test system is obtained. The amount of the enzyme of forming one micromole of hydrogen peroxide per one minute is defined to be one activity unit.

2) Effect and Substrate Specificity

The enzyme catalyzes the reaction of decomposing amadori compounds of $\alpha$-amino acids, $\beta$-amino acids, $\epsilon$-amino acids, D-amino acids and amines to form a glucosone, hydrogen peroxide and the corresponding amino acid or amine. The substrate specificity of the enzyme to essential amadori compounds is shown in Table 1 below. The enzyme not only decomposes amadori compounds of $\alpha$-amino acids but also effectively acts on other amadori compounds having fructose as bonded to amino groups as positioned in other positions than the $\alpha$-position of amino acids (for example, di-D-fructosyl-lysine, $\epsilon$-D-fructosyl-L-lysine).

Fructosylamino acid oxidase to be produced by microorganisms of belonging to the genus Corynebacterium (Japanese Patent Application Laid-Open No. 61-268178), which is known fructosylamine compounds decomposing enzyme, does not act on $\epsilon$-amadori compounds. Fructosylamine oxidase to be produced by microorganisms of belonging to the genus Aspergillus (Japanese Patent Application Laid-Open No. 3-155780) is said to act on $\epsilon$-amadori compounds, from the description of the laid-open specification, but the activity of the enzyme for acting on them is lower than that of the same for acting on $\alpha$-D-fructosyl-glycine. Fructosylamino acid decomposing enzyme to be produced by microorganisms of belonging to the genus Penicillium (Japanese Patent Application Laid-Open No. 4-4874) has a much lower activity than the enzyme of the present invention.

As opposed to the known enzymes, the enzyme of the present invention is characterized by its high activity of acting on also amadori compounds having fructose bonded to amino groups positioned in other positions than the $\alpha$-position of amino acids (for example, di-D-fructosyl-lysine, $\epsilon$-D-fructosyl-L-lysine).

The concentration of the substrate as employed for the measurement was 2 mM, except for the use of 1 mM for di-D-fructosyl-lysine.

TABLE 1

| Substrate Specificity of the Enzyme of the Invention | |
|---|---|
| Substrate | Activity of the Enzyme |
| D-fructosyl-glycine | 100 |
| D-fructosyl-L-alanine | 251 |
| D-fructosyl-D-alanine | 26 |
| D-fructosyl-$\beta$-alanine | 44 |
| D-fructosyl-L-phenylalanine | 36 |
| D-fructosyl-L-proline | 1348 |
| Di-D-fructosyl-lysine | 3500 |
| $\epsilon$-D-fructosyl-L-lysine | 1386 |
| D-fructosyl-polylysine | 34 |
| D-fructosyl-methylamine | 105 |
| D-fructosyl-sarcosine | 63 |

The data of the activity are relative values to the activity to D-fructosyl-glycine being 100.

(3) Optimum pH Range

Figure 1:
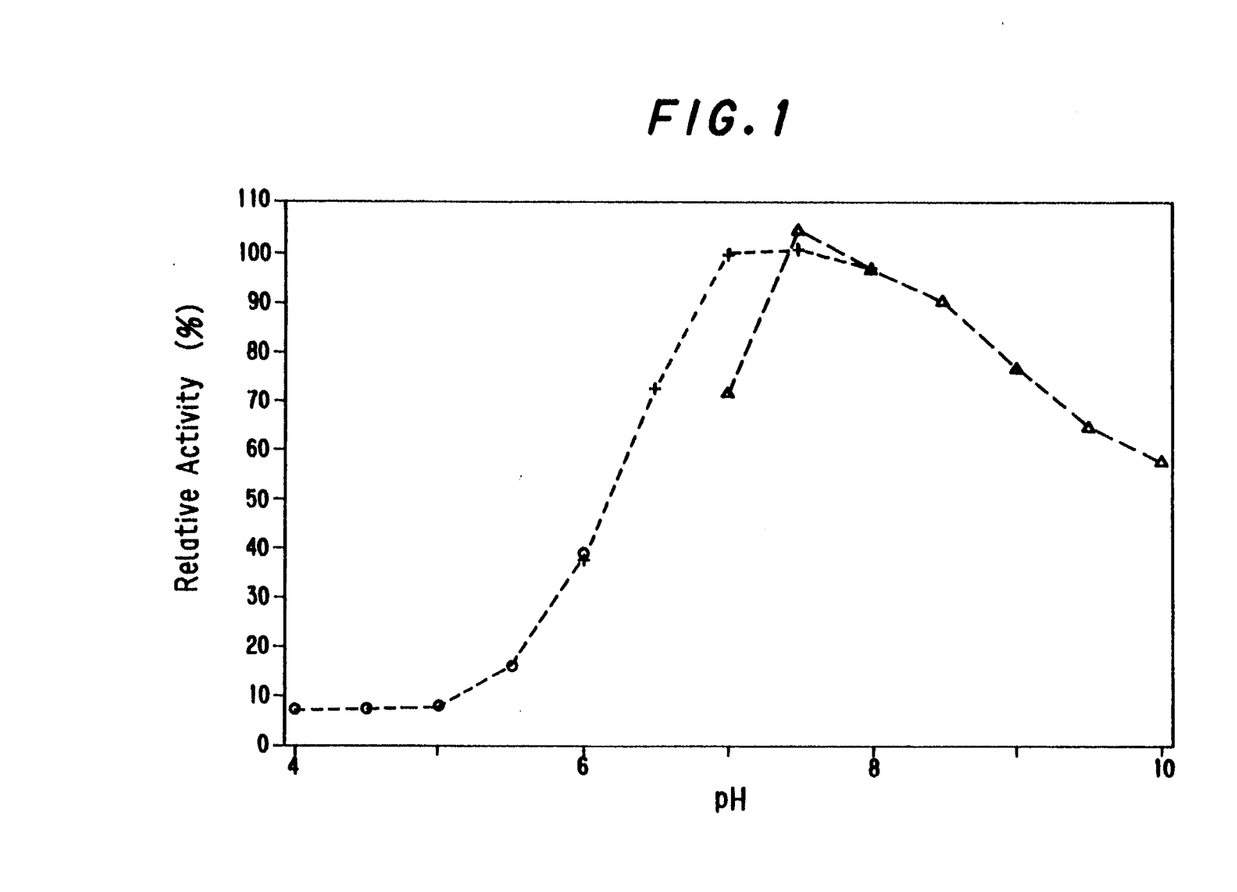
FIG. 1 is a graph to show the optimum pH of the enzyme of the present invention from the relationship between the ambient pH and the relative activity of the enzyme.

The enzyme (0.2 U) was reacted in various buffers at 37° C. for 4 minutes, and the hydrogen peroxide formed was measured by colorimetric determination to determine the activity of the enzyme. As a result, the optimum pH range of the enzyme to a substrate di-fructosyl-lysine was found to be between 7.0 and 8.0, as shown in FIG. 1 where the activity at pH 7.0 is taken as 100%. The buffers used are shown in FIG. 1 as follows:

○—○: 0.1M citrate buffer
+—+: 0.1M phosphate buffer
△—△: 0.1M tris-hydrochloric acid buffer

(4) pH Stability

Figure 2:
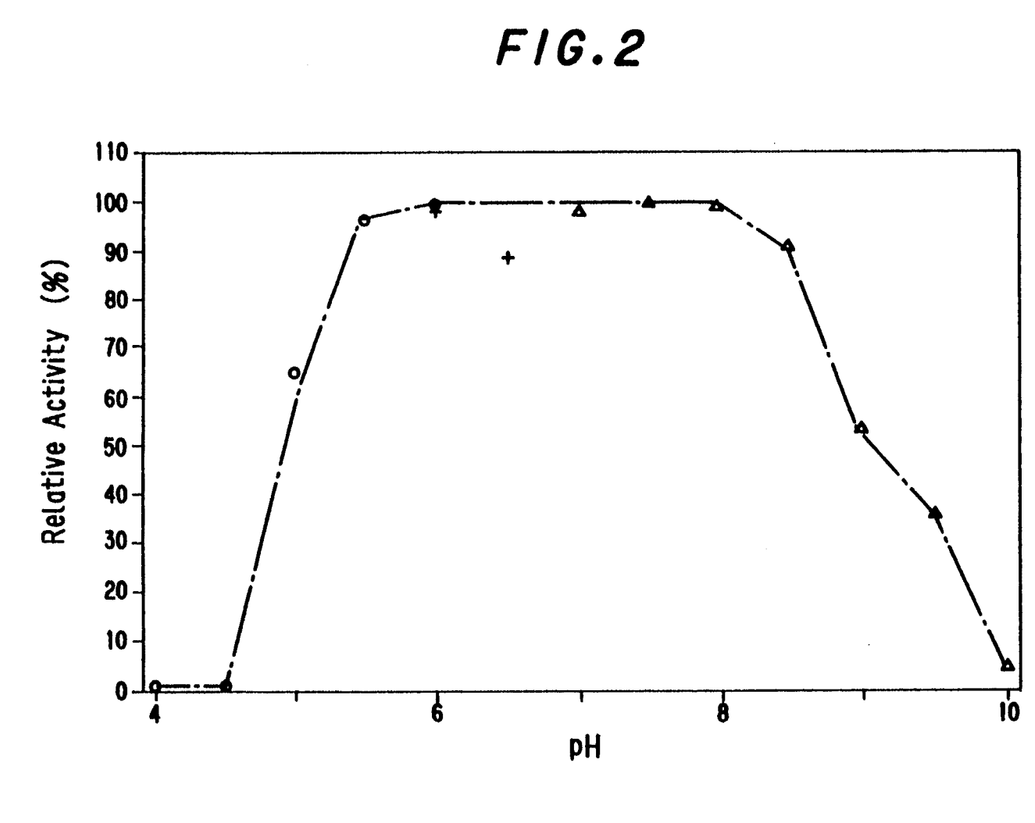
FIG. 2 is a graph to show the pH stability of the enzyme of the present invention from the relationship between the ambient pH and the relative activity of the enzyme.

Various buffers each containing the enzyme (0.2 U) were incubated at 37° C. for 10 minutes and then reacted at 37° C., whereupon the activity of the enzyme was obtained from the variation of the absorbance. The results are shown in FIG. 2 where the activity at pH 7.0 is taken as 100%. The buffers used are shown in FIG. 2 as follows:

○—○: 0.1M citrate buffer
+—+: 0.1M phosphate buffer
△—△: 0.1M tris-hydrochloric acid buffer

(5) Range of Reaction Temperature

Figure 3:
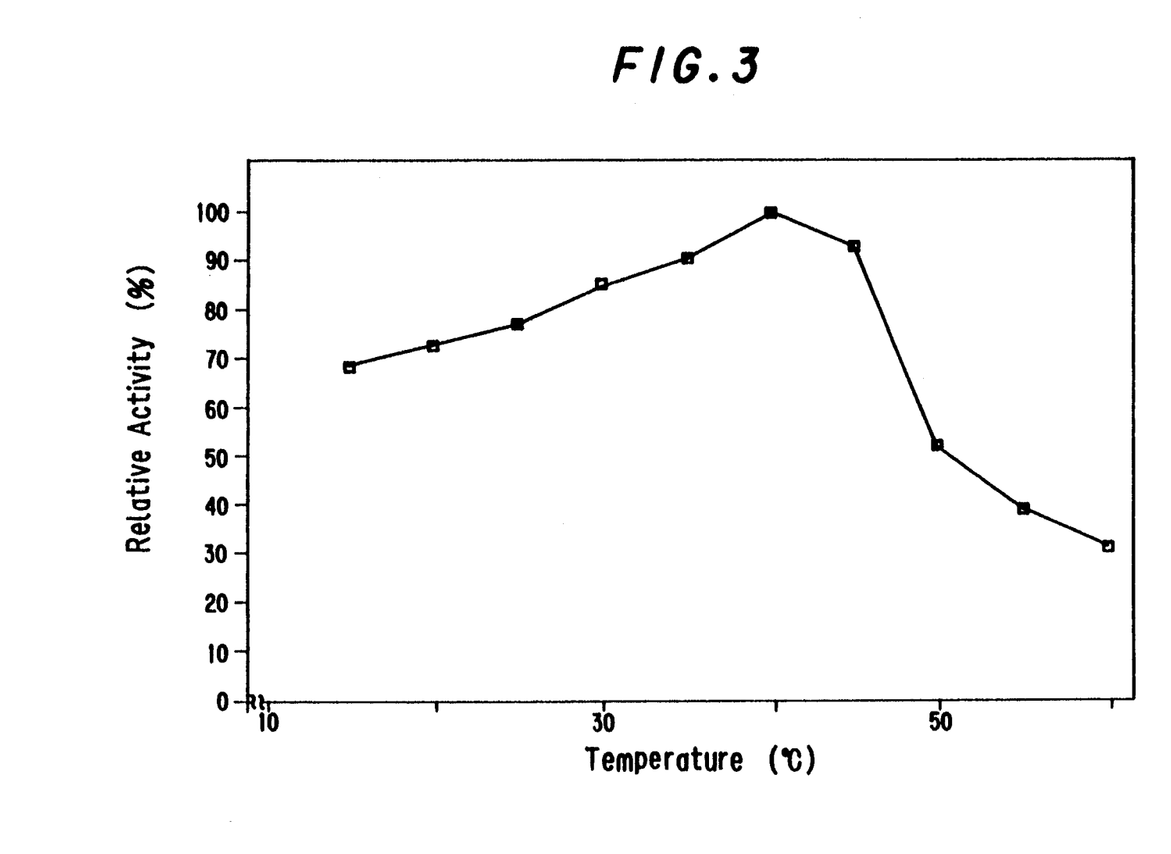
FIG. 3 is a graph to show the active temperature of the enzyme of the present invention from the relationship between the ambient temperature and the relative activity of the enzyme.

Using di-fructosyl-lysine as a substrate, the enzyme (0.3 U) was reacted in 10 mM phosphate buffer (pH 6.0) at a varying temperature for 4 minutes, whereupon the hydrogen peroxide formed was measured by colorimetric determination. The results are shown in FIG. 3 where the activity at 40° C. is taken as 100%. From this, the suitable reaction temperature of the enzyme is between 15° C. and 45° C.

Figure 4:
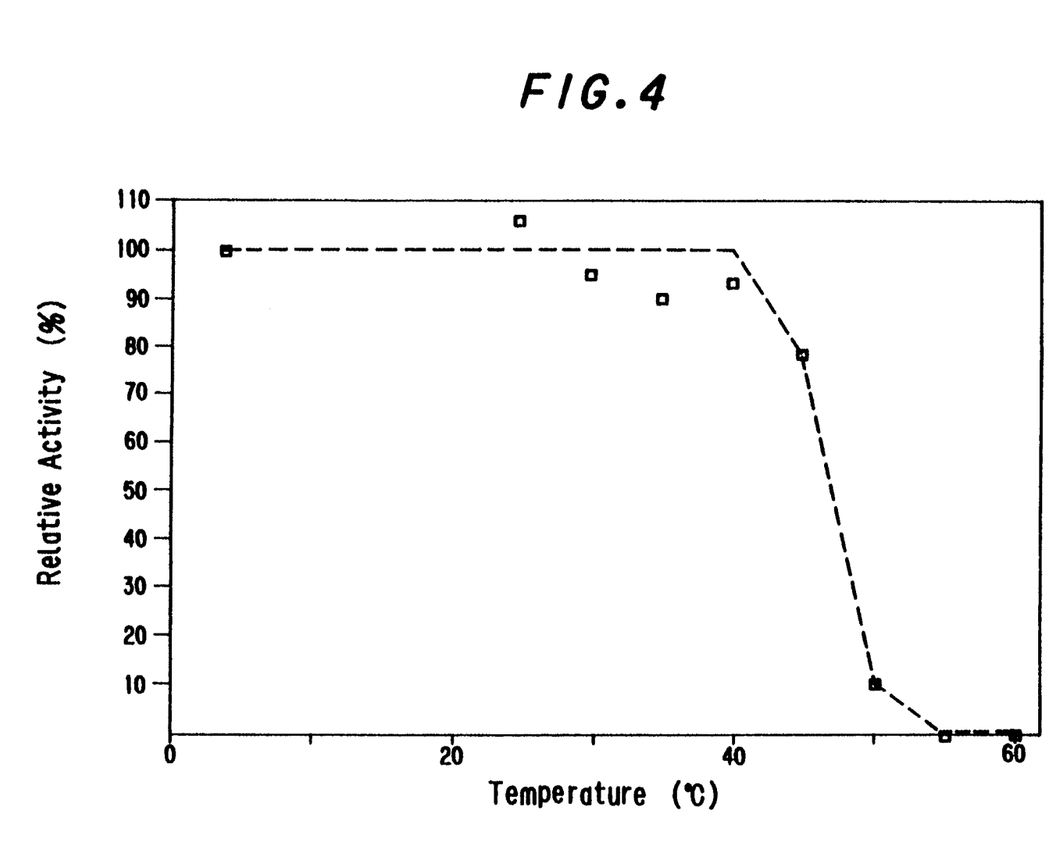
FIG. 4 is a graph to show the thermostability of the enzyme of the present invention from the ambient temperature and the relative activity of the enzyme.

(6) Thermostability 0.2 ml of 10 mM phosphate buffer (pH 6.0) containing the enzyme (0.2 U) was left at a different temperature for 10 minutes. Afterwards, 0.06 ml of the enzyme solution was reacted at 37° C. to determine the activity from the variation of the absorbance, using a substrate di-fructosyl-lysine. The results are shown in FIG. 4 where the activity after left at 4° C. for 10 minutes is taken as 100%. From this, it is noted that the enzyme is stable at a temperature of 40° C. or lower but 80% or more of it loses the activity at 50° C.

(7) Influence by Inhibitors 0.2 ml of 10 mM phosphate buffer (pH 6.0) containing the enzyme (0.2 U) was blended with a different inhibitor and reacted at 37° C. for 4 minutes, whereupon the hydrogen peroxide formed was measured by colorimetric determination. The influence of a 2 mM inhibitor on the enzyme was as follows:

The enzyme was strongly inhibited by $Cu^{2+}$, $Ni^{2+}$, $Zn^{2+}$ and $Co^{2+}$ but was not inhibited by $Mg^{2+}$. It was strongly inhibited by p-chloromercuribenzoic acid (PCMB) but was not inhibited by $NAN_3$.

(8) Method of Purification

The enzyme may be purified by the method to be mentioned hereunder.

(9) Molecular Weight

The molecular weight of the enzyme was about 43000, as measured by gel filtration with a Toyo Pearl HW-55F column. The buffer used for the measurement was 10 mM phosphate buffer (pH 6.0) containing 0.1M sodium chloride.

(10) Isoelectric Point

The isoelectric point (pI) of the enzyme was 4.8, as measured by disc isoelectric point electrography.

(11) Detection of the Purity of the Enzyme

The enzyme was subjected to electrophoresis for 2 hours, using an electrophoretic gradient gel (PAG4/15, produced by Dai-ichi Chemicals Co.) under the condition of 30 mA/gel, whereupon the enzyme protein was stained with Coomassie Brilliant Blue G-250. As a result, a single band was identified.

As mentioned above, the enzyme of the present invention is an unknown novel enzyme with respect to the effect and the substrate specificity.

As having the above-mentioned effect and substrate specificity, the enzyme was named fructosylamine deglycase.

Next, the method of producing fructosylamine deglycase of the present invention will be explained below.

Microorganisms to be employed in the present invention for producing fructosylamine deglycase are not specifically defined and may be all of those having an ability of producing fructosylamine deglycase. As specific examples of them, mentioned are microorganisms of the strain *Candida guilliermondii* 7087. Mutants or variants to be obtained by natural or artificial mutation or variation of the strain may also be employed in the present invention, provided that they have the above-mentioned ability.

The strain was one as isolated by the present inventors from the sap of an oak tree (*Quercus acutissima*) as grown in a mountain in Mie Prefecture of Japan, and the microbiological properties of it are as follows:

(1) MY medium (at 25° C.):

The growth of the cells of the strain in MY medium at 25° C. was good. After cultivation of the cells for 4 days in it under the condition by plate culture, rising colonies were obtained, which were milky white, smooth and viscous and all the edges of which were wavy.

(2) With respect to the morphological aspect of the cells, the cells had a prolonged cylindrical sausage-like form. The cells were propagated by multi-polar budding and contained small oval cells.

(3) The cells formed an oily and easily precipitating membrane.

(4) The cells formed gas from glucose.

(5) The cells were tested with Api-C-Ocsanogram (manufactured by Asuka Pure Chemicals Co.), with respect to the property of assimilating carbohydrates. The results are shown in Table 2 below.

The above-mentioned microbiological properties of the strain were investigated with reference to "The Yeast, A Taxonomic" (M. J. W. Kreger-van Rij (ed), Elsevier Science Publishers, B. V.-Amsterdam (1982)) to the result that the strain was identified to be *Candida guilliermondii*. The strain was named *Candida guilliermondii* 7087.

The strain was deposited in the Fermentation Research Institute of Japan as FERM BP-3878, deposited on Jun. 1, 1992.

TABLE 2

Assimilation of Carbohydrates by *Candida guilliermondii* 7087

| Substrate | Activity |
| --- | --- |
| Glucose | +++ |
| Glycerol | +++ |
| 2-Ketogluconic acid | +++ |
| L-arabinose | +++ |
| Xylose | +++ |
| Adonitol | +++ |
| Xylitol | +++ |
| Galactose | +++ |
| Inositol | − |
| Sorbitol | +++ |
| Methyl-D-glucoside | +++ |
| N-acetyl-D-glucosamine | +++ |
| Cellobiose | +++ |
| Lactose | − |
| Maltose | +++ |
| Saccharose | +++ |
| Trehalose | +++ |
| Melezitose | +++ |
| Raffinose | +++ |

+++: The carbohydrate was assimulated by the strain.

−: The carbohydrate was not assimilated by the strain.

The medium to be used for producing the enzyme of the present invention may be either a synthetic medium or a natural medium, which suitably contains carbon sources, nitrogen sources, inorganic substances and other nutrients and in which the above-mentioned microorganisms may grow to produce the intended enzyme.

As carbon sources, usable are, for example, saccharides such as glucose, fructose, sucrose and the like, and also natural materials containing them. As nitrogen sources, usable are, for example, inorganic ammonium salts and other nitrogen-containing organic substances such as peptone, digested products of casein, yeast extract and the like. As inorganic substances, usable are, for example, salts of magnesium, sodium, potassium, manganese, iron and the like.

In order to efficiently produce the enzyme of the present invention of fructosylamine deglycase, preferred is an addition of fructosylamino acid to the medium in cultivation of the microorganisms in it. For instance, preferred for use in the present invention is a medium containing 1% of fructosyl-lysine, 0.1% of dipotassium phosphate, 0.05% of magnesium sulfate, 0.05% of potassium chloride, 0.001% of iron(II) sulfate, 1.0% of glucose and 0.05% of yeast extract.

The cultivation temperature is suitably within the range between 25° C. and 35° C., and it is preferably about 30° C.

The pH value of the medium for cultivation is suitably within the range between 4.0 and 7.0, and it is preferably about 5.0. The cultivation time lasts until the intended enzyme is produced sufficiently. In general, it is suitably within the range between 12 hours and 36 hours.

As the way for cultivation, desired is a shaking culture or a deep agitation culture.

Next, the method of purifying the enzyme will be mentioned. Since the enzyme generally exists in the cells, the cells are collected from the culture and suspended in a suitable amount of a buffer. The cell suspension is then milled to solubilize the enzyme to obtain an enzyme-containing solution. From the thus obtained enzyme-containing solution, impurities such as nucleic acids and cell walls are removed to obtain the intended fructosylamine deglycase.

The enzyme my be isolated and purified by ordinary enzyme purification methods. For instance, employable for the isolation and purification are (1) ammonium sulfate fractionation, (2) DEAE-cellulose column chromatography, (3) phenylcellulose column chromatography, (4) hydroxyapatite column chromatography, (5) gel filtration column chromatography and the like. They may be employed singly or in combination of them. If desired, they may also be combined with any other methods. Thus, the enzyme of the present invention may be obtained as a pure product.

One example of the method of purifying the enzyme of the present invention will be mentioned.

The cells as collected from the culture are suspended in 50 mM phosphate buffer (pH 7.0) containing 5 mM EDTA, and the cells in the suspension are disrupted with a French press (produced by American Instrument Co.) under 1500 psi. This is centrifuged to collect the separated supernatant. Ammonium sulfate is added to the supernatant to have a 70% saturated concentration, for ammonium sulfate fractionation. This is centrifuged to collect the precipitates. The precipitates are suspended in a small amount of 10 mM phosphate buffer (pH 7.0) containing 1 mM EDTA, and the suspension is dialyzed against the same buffer overnight. The resulting dialysate is passed through a DEAE-cellulofine column as previously equilibrated with 10 mM phosphate buffer (pH 7.0) containing 1 mM EDTA whereby the enzyme is adsorbed to the column content. The enzyme-adsorbed column content is then washed with 10 mM phosphate buffer (pH 7.0) containing 1 mM EDTA and thereafter eluted with the same buffer having concentration gradient of from 0M to 0.1M potassium chloride, whereby the active fraction is collected. Ammonium sulfate is added to the thus obtained enzyme solution to have a concentration of 1.2M, and this is passed through a phenyl-cellulose column as previously equilibrated with 10 mM phosphate buffer (pH 7.0) containing 1.2M ammonium sulfate and 1 mM EDTA so that the enzyme is adsorbed to the column content. This is washed with the same buffer and then eluted with the same buffer having concentration gradient of from 1.2 to 0.5M ammonium sulfate, whereby the active fraction is collected. Next, the thus obtained enzyme solution is dialyzed against 10 mM phosphate buffer (pH 6.0) containing 1 mM EDTA, overnight. The dialysate enzyme solution is passed through a hydroxyapatite column as previously equilibrated with the same buffer so that the enzyme is adsorbed to the column content. This is washed with the same buffer and then eluted with the same buffer having concentration gradient of from 10 to 200 mM phosphate buffer, whereby the active fraction is collected. The active fraction thus collected is concentrated and gel-filtrated on a Toyo Pearl HW-55F column as previously equilibrated with 10 mM phosphate buffer (pH 6.0) containing 0.1M sodium chloride, whereby the intended enzyme is finally obtained as a pure product.

Next, the method of quantitative determination of amadori compounds with the enzyme of the present invention will be explained below.

The quantitative determination method of the present invention is based on the decomposition of fructosylamine compounds with the enzyme in accordance with the following reaction scheme.

$$R^1\text{—NH—CH}_2\text{—CO—}R^2 + H_2O + O_2$$
$$\rightarrow R^1\text{—NH}_2 + \text{OHC—CO—}R^2 + H_2O_2$$

In this, $R^1$ indicates a protein, a peptide chain, an amino acid or an amine residue; and $R^2$ indicates an aldose residue.

The quantitative determination method of the present invention may apply to any liquid containing the above-mentioned fructosylamine compounds. For instance, in accordance with the method of the present invention, the concentration of the fructosylamine compounds in a food preparation containing high contents of amino acids and saccharides, such as soy sauce or the like, may be quantitatively determined. A saccharified protein such as fructosamine in a living body tissue sample or the like may also be quantitatively determined by the method of the present invention, by liberating the fructosylamino acid in the sample by suitable treatment.

The enzyme to be used in the quantitative determination method of the present invention may be any of the crude enzyme as obtained by disrupting the enzyme-containing cells to solubilize the enzyme and the purified enzyme as obtained in various stages in the process of purifying the crude enzyme, provided that it has an activity of decomposing fructosylamine compounds.

Where the enzyme is applied to a sample to be examined, it is reacted with the sample at a pH of from 6.0 to 9.0 and at a temperature of 40° C. or lower, preferably at a pH of from 6.5 to 8.0 and at a temperature of from 30° to 40° C., generally for about 5 minutes. Any and every buffer which does not interfere with the activity of the enzyme used may be used in the reaction. For instance, as usable buffers, mentioned are acetic acid-sodium acetate buffer, citric acid-sodium citrate buffer, potassium phosphate buffer, tris-hydrochloric acid buffer and the like.

In accordance with the present invention, quantitative determination of amadori compounds may be effected by any of the following methods.

(1) Method of measuring the amount of hydrogen peroxide as formed by the enzymatic reaction:

Hydrogen peroxide to be formed by the reaction with the enzyme is measured by an ordinary colorimetric method, hydrogen peroxide electrode method or the like to determine the hydrogen peroxide concentration. Next, the amadori compounds are quantitatively determined from the standard curve as previously prepared to indicate the relationship between the amount of hydrogen peroxide and that of the amadori compounds. Where amadori compounds are quantitatively determined by way of a colorimetric method, the above-mentioned "method of determination of the titer of the enzyme" is referred to as one example. Where the saccharified amount of the protein in a sample from a living body is quantitatively determined, the amino acid residue of the saccharide-bonding site is previously liberated with a protease and then is reacted with the enzyme whereby the intended amount my be measured in the same manner as mentioned above.

(2) Method of measuring the amount of the oxygen as consumed by the reaction:

The amount of the oxygen to be consumed by the reaction with the enzyme is measured, and the amadori compounds are quantitatively determined from the standard curve as previously prepared to indicate the relationship between the amount of the consumed oxygen and that of the amadori compounds. Measurement of the amount of the oxygen in the reaction system may be effected by an ordinary Warburg's manometric method, oxygen electrode method or the like.

The present invention will be explained in more detail by way of the following examples, which, however, are not intended to restrict the scope of the present invention.

EXAMPLE 1

Cells of *Candida guilliermondii* 7087 (FERM BP-3878) were inoculated in a 500 ml-volume Sakaguchi flask having therein 100 ml of a medium (pH 6.8) containing 1% of di-fructosyl-lysine, 0.1% of dipotassium phosphate, 0.05% of magnesium sulfate, 0.05% of potassium chloride, 0.001% of iron(II) sulfate, 1.0% of glucose and 0.05% of yeast extract, and cultivated therein by shaking culture at 30° C. for 24 hours.

Next, the seed culture was transplanted in a 5 liter-jar fermenter having therein 3 liters of a medium having the same composition as above, and cultivated therein by deep agitation culture under the controlled condition comprising aeration of 2.5 liters/min, agitation of 400 rpm, temperature of 30° C. and pH of 5.0, for 24 hours. After cultivation, the culture was centrifuged at 6000 rpm for 10 minutes at 4° C. to collect the cells.

The cultivated cells thus obtained were suspended in 50 mM phosphate buffer (pH 7.0) containing 5 mM EDTA and disrupted with a French Press (manufactured by American Instrument Co. ) under 1500 psi. The disrupted solution was centrifuged at 12000 rpm at 4° C. for 10 minutes to collect the separated supernatant of 280 ml. Ammonium sulfate was added to the supernatant to have a 70% saturated concentration. This was allowed to stand at 4° C. for 2 hours and then centrifuged at 12000 rpm at 4° C. for 10 minutes to collect the separated precipitates.

The precipitates were suspended in a small amount of 10 mM phosphate buffer (pH 7.0) containing 1 mM EDTA and then dialyzed against the same buffer overnight. The dialysate of the enzyme solution was applied on a DEAE-cellulofine column (diameter 5 cm×10 cm) as previously equilibrated with the same buffer so that the enzyme was adsorbed to the column content. Next, this was eluted with the same buffer having concentration gradient of from 0M to 0.1M potassium chloride to collect the active fraction. Ammonium sulfate was added to the enzyme-containing active fraction to have a concentration of 1.2M, and this was applied on a phenyl-sepharose column (diameter 5 cm×5 cm ) as previously equilibrated with 10 mM phosphate buffer (pH 7.0) containing 1.2M ammonium sulfate and 1 mM EDTA so that the enzyme was adsorbed to the column content. This was then eluted with the same buffer having concentration gradient of from 1.2M to 0.5M ammonium sulfate to collect the active fraction. The enzyme-containing active fraction was then dialyzed against 10 mM phosphate buffer (pH 6.0) containing 1 mM EDTA, overnight. The enzyme-containing dialysate was applied on a hydroxyapatite column (diameter 5 cm×5 cm) as previously equilibrated with the same buffer so that the enzyme was adsorbed to the column content. This was then eluted with the same buffer having concentration gradient of from 10 mM to 200 mM phosphate buffer to collect the active fraction.

The thus obtained active fraction was concentrated with an ultrafiltration device ( fractionation membrane: molecular weight of 10,000) (manufactured by Amicon Co. ) and then gel-filtrated on a Toyo Pearl HW-55F column (diameter 2 cm×70 cm) as previously equilibrated with 10 mM phosphate buffer (pH 6.0) containing 0.1M sodium chloride. The isolated active fraction was collected to obtain an enzyme solution of 50.4 units. The yield was 12.2%.

EXAMPLE 2

20 ml of an aqueous solution (pH 6.8) containing 15% of glucose and 5% of lysine was heat-treated at 121° C. for 15 minutes, and was added to a 500 ml-volume Sakaguchi flask containing therein 80 ml of a medium (pH 6.8) containing 0.125% of dipotassium phosphate, 0.063% of magnesium sulfate, 0.063% of potassium chloride, 0.0013% of iron(II) sulfate and 0.063% of yeast extract. Cells of *Candida guilliermondii* 7087 (FERM BP-3878) were inoculated in it and cultivated therein by shaking culture at 30° C. for 24 hours.

Next, the seed culture was transplanted in a 5 liter-jar fermenter having therein 3 liters of a medium having the same composition as above, and cultivated therein by deep agitation culture under the controlled condition comprising aeration of 2.5 liters/rain, agitation of 400 rpm, temperature of 30° C. and pH of 5.0, for 24 hours. After cultivation, the culture was centrifuged at 6000 rpm for 10 minutes at 4° C. to collect the cells.

The cultivated cells thus obtained were suspended in 50 mM phosphate buffer (pH 6.0) containing 5 mM EDTA and disrupted with a Daino Mill (container content: 0.6 liter, beads: diameter of 0.25 to 0.5 mm) (manufactured by Simmal Enterprise Co. ) under the condition of a flow rate of 10 liter/hr. The disrupted solution was centrifuged at 12000 rpm at 4° C. for 10 minutes to collect the separated supernatant of 1400 ml. Ammonium sulfate was added to the supernatant to have a 30% saturated concentration. This was allowed to stand at 4° C. for 2 hours and then centrifuged at 12000 rpm at 4° C. for 10 minutes to collect the supernatant.

Ammonium sulfate was added to the supernatant to have a 70% saturated concentration. This was allowed to stand at 4° C. for 2 hours and then centrifuged under the same condition as above to collect the separated precipitates. The precipitates were suspended in a small amount of 10 mM phosphate buffer (pH 6.0) containing 1 mM EDTA and then dialyzed against the same buffer, overnight. The dialysate of the enzyme solution was applied on a DEAE-cellulofine column (diameter 5 cm×10 cm) as previously equilibrated with the same buffer so that the protein impurities were adsorbed to the column content and the non-adsorbed active fraction was collected.

Next, the enzyme-containing fraction was applied on a hydroxyapatite column. (diameter 5 cm×5 cm) as previously equilibrated with 10 mM phosphate buffer (pH 6.0) containing 1 mM EDTA so that the enzyme was adsorbed to the column content. This was then eluted with the same buffer having concentration gradient of from 10 mM to 200 mM phosphate buffer to collect the active fraction.

The thus obtained active fraction was concentrated with an ultrafiltration device (fractionation membrane: molecular weight of 10,000) (manufactured by Amicon Co. ) and then gel-filtrated on a Toyo Pearl HW-55F column (diameter 2 cm×70 cm) as previously equilibrated with 10 mM phosphate buffer (pH 6.0) containing 0.1M sodium chloride. The isolated active fraction was collected to obtain an enzyme solution of 153 units. The yield was 27.6%.

EXAMPLE 3

0.4 ml of 0.05M phosphate buffer (pH 7.0) containing 0.3 mM 4-aminoantipyrine, 0.5 mM TOOS and 2.0 U/ml peroxidase was added to 0.1 ml of di-fructosyl-lysine of from 0.025 to 1.0 mM (as dissolved in 50 mM phosphate buffer of pH 7.0), and the temperature of it was equilibrated at 37° C.

Figure 5:
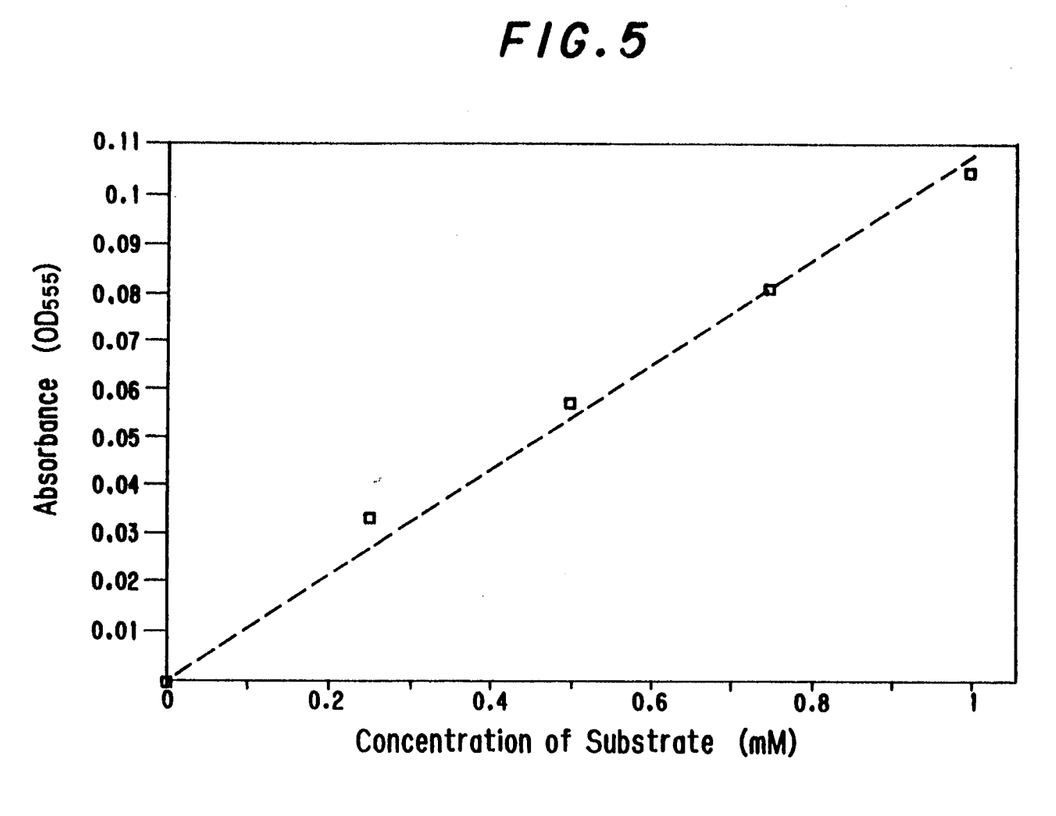
FIG. 5 is a graph to show the relationship between the concentration of the enzyme of the present invention and the absorbance of the same.

0.05 ml of the enzyme having an activity of 0.2 U/ml was added to this, whereupon the variation of the absorbance for 2 minutes at 555 nm was measured with a spectrophotometer (U-2000 Model, manufactured by Hitachi Ltd. ) at regular intervals of 20 seconds and the variation of the absorbance per one minute was obtained. As a result, the proportional relationship between the concentration of di-fructosyl-lysine and the absorbance was identified, as shown in FIG. 5. From this, the quantitative determination of the amadori compounds was verified.

EXAMPLE 4

The saccharified amount of the protein in a serum was measured by the method mentioned below.

(1) Decomposition of serum protein:

10,000 U of a pre-treating reagent Pronase (produced by Wako Pure Chemicals Co.) was dissolved in one liter of 10 mM phosphate buffer (pH 7.0) to prepare a reagent solution (1).

(2) Reagent for colorimetric determination:

0.3 mM 4-aminoantipyrine (produced by Wako Pure Chemicals Co.), 0.3 mM TOOS (produced by Dotite Co.) and 2 U/ml peroxidase (produced by Katayama Chemicals Co.) were dissolved in 50 mM phosphate buffer (pH 7.0), and 1U/ml, as the final concentration, of the fructosylamine deglycase of the invention was added to the resulting solution to prepare a reagent solution (2).

(3) Measuring method:

200 μl of the reagent solution (1) was added to 10 μl of a human serum sample with stirring and kept at 37° C. for 5 minutes. Subsequently, 200 μl of the reagent solution (2) was added thereto with stirring, whereupon the absorbance at 545 nm of the sample was measured with a spectrophotometer (U-2000 Model, manufactured by Hitachi Ltd.) in one minute and in 5 minutes at 37° C. The variation of the absorbance indicates the measured value of the sample.

By the method mentioned above, 100 serum samples taken from diabetics and healthy panelists were examined.

All the serum samples were previously examined with respect to the saccharified amount by a known fructosamine method (using a fructosamine measuring kit of NEW Glyca P, manufactured by Chugai Pharmaceutical Co.).

Figure 6:
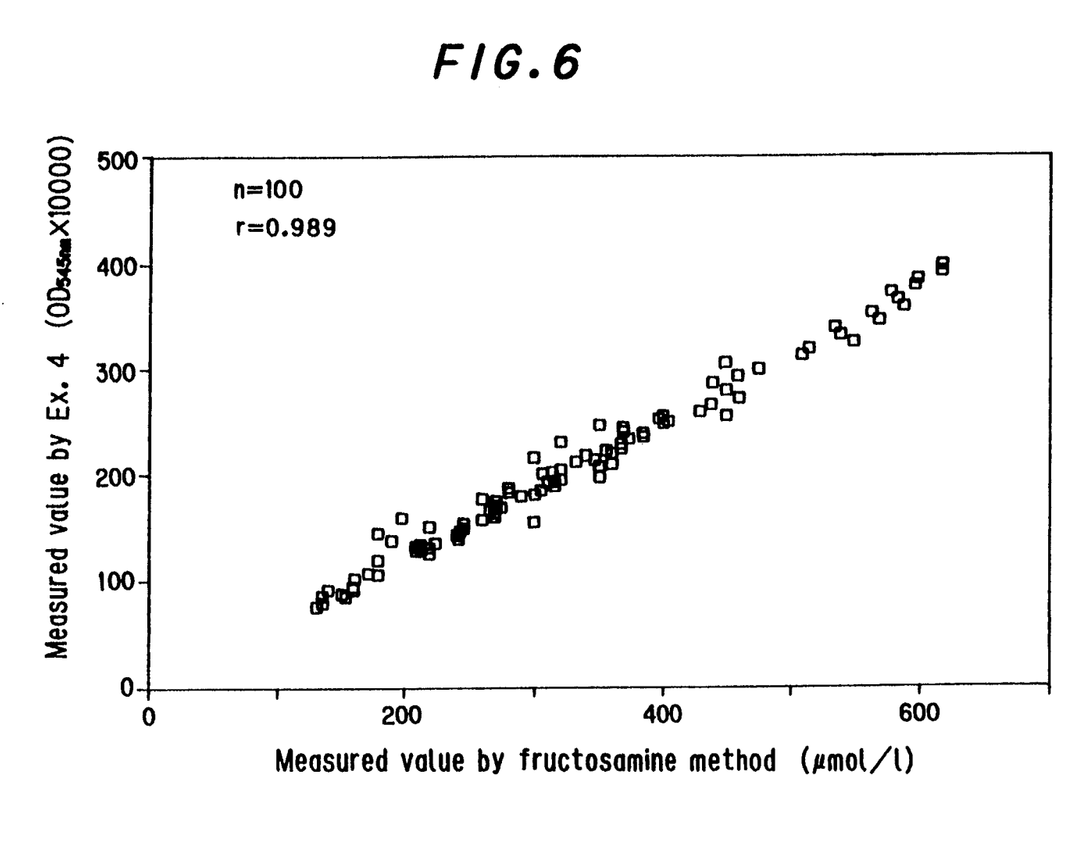
FIG. 6 is a graph to show the relationship between the results of measurement by the present invention and the results by chemical measurement.

The results are shown in FIG. 6, which demonstrates that the enzymatic measuring method of using the enzyme of the present invention has a significant relationship to the chemical measuring method of a known fructosamine method.

Thus, the present example has verified the quantitative determination of the saccharified amount of the protein in a sample from a living body with the enzyme of the present invention, by application of a suitable protein decomposition treatment with a protease to the sample.

As explained above in detail, the present invention provides a novel enzyme characterized by the high specificity to the reaction with amadori compounds, especially that having therein a saccharide moiety as bonded to the ε-amino group, and also provides a method of producing the enzyme and a method of quantitative determination of amadori compounds with the enzyme. Using the enzyme of the present invention, quantitative determination of amadori compounds, which has heretofore been difficult by conventional enzymatic methods, is possible with ease.

In particular, in measurement of the amount of a saccharified protein in a sample from a living body, which is an important index substance in the diagnosis of diabetes, the enzymatic method of the present invention of measuring fructosamine in the sample is hardly influenced by other interfering substances or impurities in the sample, the influence by them having been inevitable in conventional chemical methods. Accordingly, accurate determination of the amount is possible by the method of the present invention. In addition, the method of the present invention is free from the inconvenience of staining the kits and instruments used.

For measuring glycohemoglobin, the method of the present invention displays another characteristic feature that the operation of the method is more simple and needs less labor and time than conventional methods.

While the invention has been described in detail and with reference to specific embodiments thereof, it will be apparent to one skilled in the art that various changes and modifications can be made therein without departing from the spirit and scope thereof.

What is claimed is:

1. A fructosylamine deglycase having the following physico-chemical properties:
    (a) effect and substrate specificity: the fructosylamine deglycase acts on amadori compounds, especially effectively on an ε-amino acid amadori compound to catalyze oxidation of the amadori compounds to produce an α-ketoaldehyde, an amine compound and hydrogen peroxide;
    (b) optimum pH and pH stability: the fructosylamine deglycase is stable at a pH of 5.0 to 8.0 with respect to a substrate of di-fructosyl-lysine, and having an optimum pH with respect to the substrate of 7.0 to 8.0 in a phosphate buffer;
    (c) range of reaction temperature: the range of the reaction temperature of the fructosylamine deglycase is 15° to 45° C.;
    (d) thermostability: the fructosylamine deglycase is stable to heat treatment of 40° C. for 10 minutes, and when the fructosylamine deglycase is heated at 50° C. for 10 minutes, 80% or more of the fructosylamine deglycase is inactivated;
    (e) molecular weight: the fructosylamine deglycase has a molecular weight of about 43000, as measured by gel filtration on a column of a porous, semirigid, spherical gel.

2. The fructosylamine deglycase of claim 1, having an isoelectric point of 4.8, as measured by disc isoelectric point electrography.

3. A method of producing a fructosylamine deglycase of claim 1, comprising
    (a) cultivating microorganism *Canada guilliermondii* FERM BP-3878, said microorganism having a capacity of producing the fructosylamine deglycase, in a medium and
    (b) collecting the produced fructosylamine deglycase from the culture.

4. The method of claim 3, wherein the cultivating is carried out at a temperature of 25° C. to 35° C. at a pH of 4.0 to 7.0 for 12 hours to 36 hours.

5. The method of claim 4, wherein the temperature is 30° C. and the pH is 5.0.

* * * * *

UNITED STATES PATENT AND TRADEMARK OFFICE
CERTIFICATE OF CORRECTION

PATENT NO.   : 5,387,109
DATED        : February 7, 1995
INVENTOR(S)  : ISHIKAWA et al It is certified that error appears in the above-indentified patent and that said Letters Patent is hereby corrected as shown below:

Column 14, line 26, claim 3:   delete "*Canada*" and
                       insert --*Candida*--.

Signed and Sealed this

Ninth Day of April, 1996

Attest:

BRUCE LEHMAN

Attesting Officer

Commissioner of Patents and Trademarks